United States Patent [19]

Sweetana et al.

[11] Patent Number: 5,183,760
[45] Date of Patent: Feb. 2, 1993

[54] APPARATUS FOR IN VITRO DETERMINATION OF SUBSTANCES ACROSS MEMBRANES, BIOLOGICAL TISSUES, OR CELL CULTURES

[76] Inventors: Stephanie A. Sweetana; George M. Grass, both of 101 First St., Los Altos, Calif. 94022

[21] Appl. No.: 685,167

[22] Filed: Apr. 12, 1991

Related U.S. Application Data

[63] Continuation of Ser. No. 354,479, May 19, 1989, abandoned.

[51] Int. Cl.$^5$ .................. C12H 1/12; G01N 15/08; G01N 13/04
[52] U.S. Cl. .................................. 435/285; 435/311; 210/612; 210/621; 210/321.72; 210/321.75; 73/38; 73/64.47
[58] Field of Search ............... 435/284, 285, 283, 813, 435/311; 210/612, 621, 646, 321.75, 321.72, 645; 73/38, 64.3

[56] References Cited

U.S. PATENT DOCUMENTS

| | | | |
|---|---|---|---|
| 3,186,917 | 6/1965 | Gerhardt et al. | 435/813 X |
| 3,386,912 | 6/1968 | Lazare | 210/321.71 |
| 3,508,656 | 4/1970 | Serfass et al. | 210/321.75 |
| 3,520,803 | 7/1970 | Iaconelli | 210/321.75 |
| 3,963,613 | 6/1976 | Chibata et al. | 435/283 X |
| 4,087,327 | 5/1978 | Feder et al. | 435/285 |
| 4,661,458 | 4/1987 | Berry et al. | 435/284 |
| 4,667,504 | 5/1987 | Hobson . | |
| 4,938,931 | 7/1990 | Cussler | 435/285 |

OTHER PUBLICATIONS

Grass et al., Pharm. Res. 5(6), pp. 372-376 (1988).
Fink et al., (1975) in Membrane Separations in Biotechnology McGregor (eds.) p. 284, Fig. 19 © 1986.
Steiber et al., (1977) in Membrane Separations in Biotechnology, McGregor (eds.) p. 286, Fig. 21 © 1986.
Vssing & Zehrahn, Acta Physiol. Scand. 23:110-127 (1951).
Schoenwald & Huang, J. Pharm. Sci., 72:11 (1983).
Hidalgo et al., Gastroentazology 78:4 (1989).

*Primary Examiner*—James C. Housel
*Assistant Examiner*—William Chan

[57] ABSTRACT

An apparatus for determining transport characteristics across membranes and tissue sections comprises a plurality of cell blocks, where each cell block includes a pair of half-cells which hold the membrane or tissure section therebetween. A circulation path is provided in each half-cell block for exposing a fluid to one side of the membrane or tissue section. The cell blocks are maintained linearly within a base unit including a front plate and a back plate. The front and back plates are heated to maintain the cell blocks at a desired temperature.

15 Claims, 3 Drawing Sheets

APPARATUS FOR IN VITRO DETERMINATION OF SUBSTANCES ACROSS MEMBRANES, BIOLOGICAL TISSUES, OR CELL CULTURES

This is a continuation division of application Ser. No. 07/354,479, filed May 19, 1989, now abandoned.

BACKGROUND

1. Field of the Invention

The invention relates to laboratory apparatus used in the measurement of transport of substances across membranes, for example, membranes of biological tissues, or a thin section or sheet of a synthetic material, and tissue or cell cultures on a support therefor.

2. Description of Related Art

Hobson, U.S. Pat. No. 4,667,504 issued May 26, 1987 discloses an apparatus for determining in vitro the penetration rate of chemicals across a biological membrane. The apparatus comprises two housings, one holding a reservoir of test chemical, and the other providing a chamber for flowing receptor solution across a membrane held in a membrane holding compartment. The membrane holding compartment comprises a cylindrical depression surrounding an open end of the receptor solution chamber. The receptor solution chamber is tilted slightly with its higher end open to the membrane holding compartment. The tile prevents bubbles in the receptor solution from becoming stalled or strapped inside the chamber and interfering with the reliability and reproducibility of tests. An inlet bore from the upper surface of the receptor housing leads to a closed end of the chamber near the membrane holding compartment to the upper surface of the receptor housing. The inlet bore is sized smaller than the outlet bore. The depth of the depression forming the membrane holding compartment varies, tapering from a lesser depth at its intersection with the chamber to a greater depth at the outer circumference of the depression. The thus formed truncated cone ensures that a sample biological membrane is stretched taut over the chamber opening by the force fastening the reservoir housing to the receptor solution housing.

The publication of Ussing and Zerahn (Acta Physiol. Scand. 23:110-127(1951) describes an apparatus for the determination of sodium flux and short circuit current in frog skin. The device has an area for placement of the skin between two opposing half cells, pressed against the skin by two lucite screws held by steel uprights. The tips of the lucite screws are conical and fit into conical depressions in the center of the ebonite dishes. Buffer solutions are circulated and aerated by air entering through side tubes. Bridges, held in position by pieces of rubber tubing, fit tightly into short celluloid side tubes sealed into the two chambers and these connect to a reservoir system. The device is also fitted with a series of electrodes.

Schoenwald and Huang (J. Pharm. Sci., 72:11 (1983)) discloses a device for mounting of corneas to determine transport of material across corneal tissue. The system is composed of two acrylic plastic blocks. Each block acts as an opposing half cell with and area for the corneal tissue between. The cornea is mounted using a system of three rings, and the ring system with the cornea is positioned in the opening of the blocks and form a watertight seal when sufficient lateral pressure is applied to the blocks in a manner similar to that described above by Ussing and Zehran. Fluid reservoirs on each side of the tissue are mixed with a gas lift mechanism, also similar to Ussing and Zehran above. Stirring motors mounted on the blocks, connect by shafts with blades on the terminus, through the block to the reservoir at the tissue face. These blades promote mixing at the tissue surface. The reservoirs are heated by circulation of temperature controlled fluid through channels in the block. The fluid reservoirs and fluid circulation channels for temperature control are within the same contiguous block.

Hildago et. al., (Gastroenterology 96:736-49 (1989)), disclose a method for the measurement of transport of material across a monolayer formed by cultured cells. Cells are grown in an appropriate media in a plastic cylinder which is caped at one end with a filter membrane. When the cells reach a confluent monolayer, the cells and the cylinder with attached filter are placed in another larger diameter cylinder with fluid which acts as the receiver solution. Materials placed in the smaller cylinder, with the cells are transported across the cells and the filter membrane to the reservoir solution of the larger cylinder.

Grass and Sweetana (Pharm. Res., 5:6 (1988) disclose a diffusion cell (chamber) for the measurement of tissue permeability. The apparatus is comprised of at least one chamber with a first and a second volume element, each of which contains a reservoir for fluids and a means to circulate fluids. Also included is a means to retain a membrane separating the first and second volume elements whereby the fluid contained in the reservoir in the first volume element housing could communicate with the fluid contained the reservoir in the second volume element in the absence of the membrane. Also included are a membrane separating the first and second volume elements, a means to circulate fluid contained in each of the first and second volume elements, and a means to attach the first and second volume elements on a contiguous surface of each of the first and second volume elements in an adjacent facing relationship, wherein the first and second volume element housings are separated from each other at their contiguous surfaces by the membrane.

The disclosure of the above publications is incorporated herein by reference

Measurement of the transport properties of molecules through various barriers is often conducted in an in vitro experiment using a device such as one of those described above. Devices which expedite the experimental process are advantageous. Such devices can relate to the measurement of transport properties through biological tissue, cell cultures, or synthetic membranes. Most commonly, the use of a side-by-side type of diffusion apparatus or cell is used. By the expression "side-by-side" type of diffusion apparatus (or cell) is meant an apparatus having two housing elements separated by the tissue or membrane to be tested.

For biological tissues, it has been possible to use the device and method of Ussing and Zehran described above. This method has certain disadvantages. The method of Ussing and Zehran uses a device which is usually comprised of several different materials all of which are in contact with the circulating fluids. Generally it is accepted that contact with as few materials as possible is preferred. Additionally, the design of the Ussing system and similarly derived designs, incorporate a temperature control means as an integral part of the fluid reservoirs, but this temperature control means does not directly encompass the tissue containing sections of the device, where the experiments actually take place. Thus, the environment of the chamber on which the experiment takes place is prone to fluctuate with respect to temperature. Furthermore, the Ussing chamber requires that the connecting tubing be disconnected, or that cleaning be done individually within the reservoir units.

Also, the Ussing device (apparatus) and those other devices derived from the Ussing device frequently allow the entrapment of bubbles in the device, with elimination of these bubbles sometimes being quite difficult. These bubbles can affect the experiment, especially if they are adjacent to the tissue surface. This is most frequent, although not limited to horizontally mounted tissues.

Another problem associated with known devices is a more technical problem relating to mixing and fluid flow within the chambers. Fluid mixing is generally recognized to be critical to the outcome of many of these types of experiments. In such known devices, mixing is accomplished by a variety of mechanisms, including stirring rod, or bars, or gas lift as described above. Such previous designs have created turbulent flow patterns, or those which directly impact on the tissue causing potentially accelerated damage.

Thus there is a need for an improved device (or apparatus) for use in in vitro experiments to test for transport of materials across tissues and synthetic membranes and cultured cells.

SUMMARY OF THE INVENTION

The apparatus of this invention is comprised of at last one chamber with a first and a second volume element, each of which contains a reservoir for fluids and a means to circulate fluids. The apparatus of this invention further comprises a means adapted to retain a membrane separating the first and second volume elements whereby the fluid contained in the reservoir in the first volume element housing could communicate with the fluid contained the reservoir in the second volume element in the absence of the membrane. Optionally, the apparatus of this invention further comprises a membrane separating the first and second volume elements. Also optionally, the apparatus further comprises temperature control means.

In another aspect, this invention is a method to determine the transport of substances across a membrane comprising one of a biological tissue, a thin sheet or section of synthetic material, and cultured tissue or cells and support therefor.

Figures 1A, 1B:
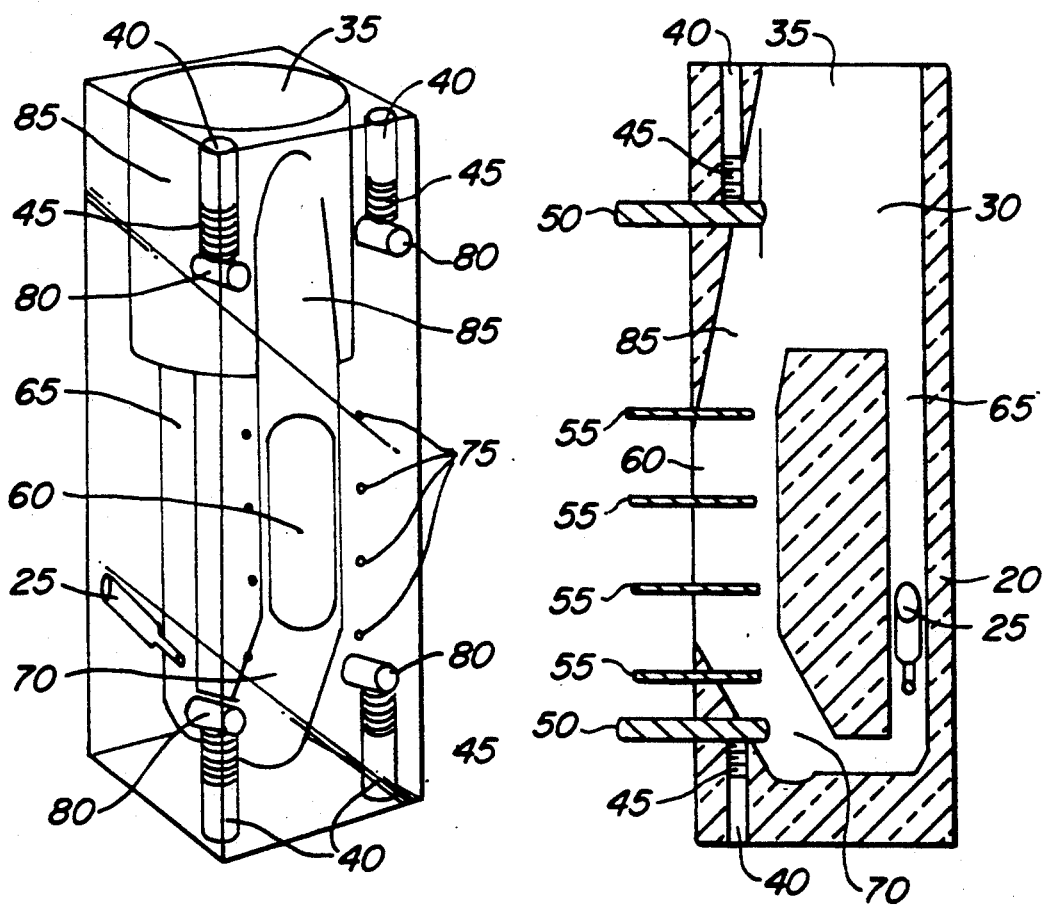
FIGS. 1A and 1B show views of a single diffusion cell with the individual half-cells separated. The left half cell of FIG. 1A shows a perspective view of the tissue opening. The right half-cell of FIG. 1B shows a side view.

Drawing Reference Numerals
20 diffusion cell block
25 inlet for gas
30 donor reservoir
35 reservoir opening
40 threaded shaft for locking screw
45 locking screw
50 joining pin
55 tissue mounting pins
60 tissue opening
65 up-flow tube for fluid flow and gas
70 lower down flow tube for fluid
75 drilled holes to match 55
80 drilled holes to match 50
85 upper down-flow tube
100 assembled diffusion cell
105 inner threaded shaft for 130
110 heating unit back plate
115 heating unit lower plate
120 barbed fitting for 125
125 fluid carrying tubing
130 front plate attachment knobs and screws
135 heating unit front plate
140 heating unit fluid channels
145 fluid channel plug
150 front plate attachment screw

DETAILED DESCRIPTION OF THE INVENTION

As described above, this invention is an apparatus useful as a diffusion cell comprising at least one chamber comprising (i) a first and a second volume element (or volume housing), each of which contains (a) a reservoir for fluids, (b) a means to circulate fluids, and (c) a means adapted to retain a membrane covering an opening and thereby separating the first and second volume elements whereby the fluid contained in the reservoir in the first volume element could communicate with the fluid contained in the reservoir in the second volume element in the absence of said membrane, (ii) a means to circulate fluid contained in each of the first and second volume elements, (iii) a means to attach the first and second volume elements on a contiguous surface of each of the first and second volume elements in an adjacent facing relationship, wherein the first and second volume elements are separated from each other at their contiguous surfaces by a membrane.

The chamber(s) according to this invention can be made of (i.e., composed of) a material selected from glass, plastics such as these commonly used for such devices such as polymethylmethacrylate, metal such as those commonly used for laboratory devices such as steel or aluminum as examples. Other included material are nylon, teflon, polycarbonate resins (such as Lexan ®, General Electric Co., Polymers Product Dept.) or methylmethacrylate resins (such as Lucite ®, DuPont).

The temperature control means, when present, comprises a holding assembly for the apparatus, the holding assembly having a back plate and a bottom plate and means to hold the apparatus in contact with the holding apparatus, at least on of the back plate and the bottom plate having (1) channels through which a fluid maintained at a predetermined temperature can be circulated, or (2) having means to be temperature controlled by electrical means, in either case the back plate and the bottom plate being produced from materials which are temperature conductive. The holding device assembly having temperature control means is generally used in the operation of the apparatus. The holding assembly having external temperature control means is composed of a material selected from glass, plastic such as these commonly used for such devices such as polymethylmethacrylate, metal such as those commonly used for laboratory devices such as steel, copper, or aluminum as examples. Other included material are nylon, teflon, Lexan TM, or Lucite TM. Alternatively, the apparatus may have as the temperature control means a thermocouple device.

As described above, the membrane may be selected from a thin sheet of biological tissue for example intestinal tissue (Grass and Sweetana, above)) or corneal tissue. Alternatively, a thin sheet or section of synthetic material may be used as the membrane. Examples of suitable material include hydrogels or silicone polymers, or such polymers as used in development of coating materials or packaging materials. In yet another alternative, cultured tissue or cultured cells grown on a suitable support may be used as the membrane (Hidalgo et al., above))

FIG. 1 shows a separated diffusion cell according to the preferred embodiment of the invention for use with intestinal tissue as previously described by Grass and Sweetana (above). The diffusion cell comprises two halves of block 20 which are preferably made of glass or plastic such as lucite or plexiglas. Each block is about 1.5 to 5 inches in height, 0.5 to 3 inches in width and 0.5 to 3 inches in depth. One half-cell is embedded with tissue mounting pins 55 preferably of metal or plastic protruding 0.2 to 5 mm, arranged around the tissue opening 60. Fluid, generally a salt containing buffer, circulates in the half-cell from the donor reservoir 30 down the upper down-flow tube 85 across the tissue mounted in the tissue opening 60. Fluid drains via the lower down tube 70 to the up-flow tube 65 where it is propelled by gas lift from the gas inlet port 25. In the preferred embodiment, this flow is laminar and parallel to the plane of the tissue. The tissue opening can be varied to accommodate different tissue sizes but is preferably between 0.25 and 5 $cm^2$ in area. The total fluid volume of each half-cell can be between 1 and 100 ml with 1 to 7 ml preferred.

The corresponding half-cell is similar except that it is designated as the receiving reservoir 85. Fluid flows from this reservoir within the half-cell in the same manner as in the donor half-cell. In the preferred embodiment, the receiver cell has drilled holes 75 to accommodate the tissue mounting pins 55.

When a tissue sample of 0.2 to 100 $cm^2$ is mounted on the pins 60, the half cells are joined in a manner such that there is no direct communication between the fluid areas, without passage through the tissue. Fluid from each half-cell can be sampled from the reservoir openings 35 which are 0.25 to 2 inches in diameter.

To hold the cells together, the joining pins 50 of metal or plastic are inserted into the mating drilled holes 80 in the opposite half-cell. To retain the pins 50 and lock the half-cell together, the locking screws 45 of metal or plastic are turned within their threaded shafts 40.

Figure 4:
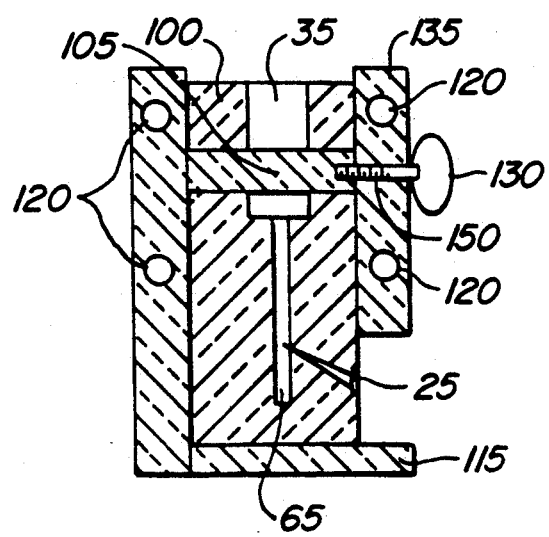
FIG. 4 is a side view of a diffusion cell in the heating unit with the front plate in its operational position.
Figure 2:
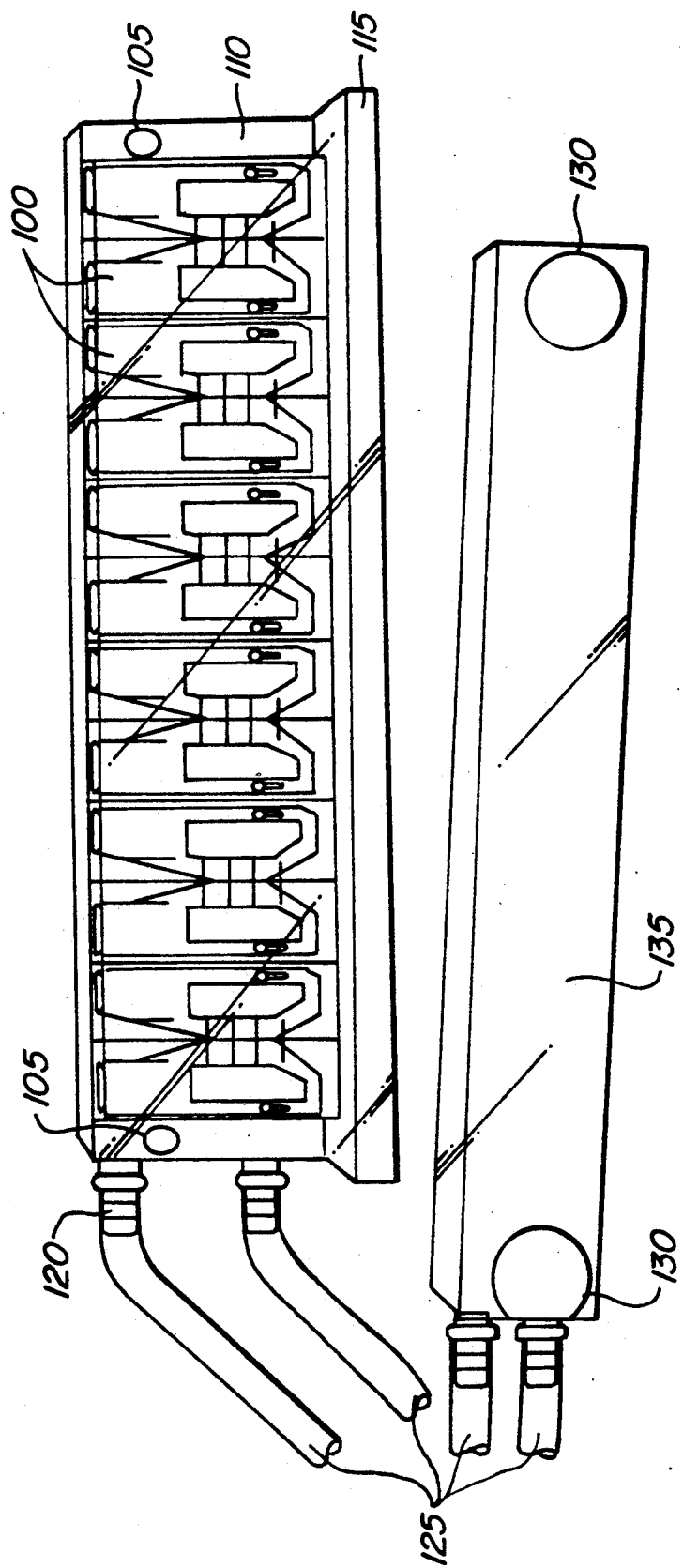
FIG. 2 shows six diffusion cells in a heating manifold. The cells are shown in front view within the back and bottom of the heating unit. The front plate is removed.

The combined half-cells form an assembled diffusion cell 100 which can be placed in a heating unit. In the preferred embodiment, the heating unit is of proportions which can accommodate multiple diffusion cells as shown in FIG. 2 and the heating plates 110, 115, and 135 are composed of a temperature conductive material. The material can be glass, plastic, or metal, with steel, copper, or aluminum preferred. The diffusion cells 100 sit on the heating unit lower plate 115 and are adjacent to the heating unit back plate 110. In the operating mode, the heating unit front plate 135 fits across the surface of the diffusion cells 100. The front plate 135 is tightened against the diffusion cells 100 using knobs 130 of metal or plastic to turn screws 150 (FIG. 4) in the holes of the threaded shaft 105 of metal or plastic. FIG. 4 shows a side view of the diffusion cell in the heating unit with the front plate attached.

Figure 3:
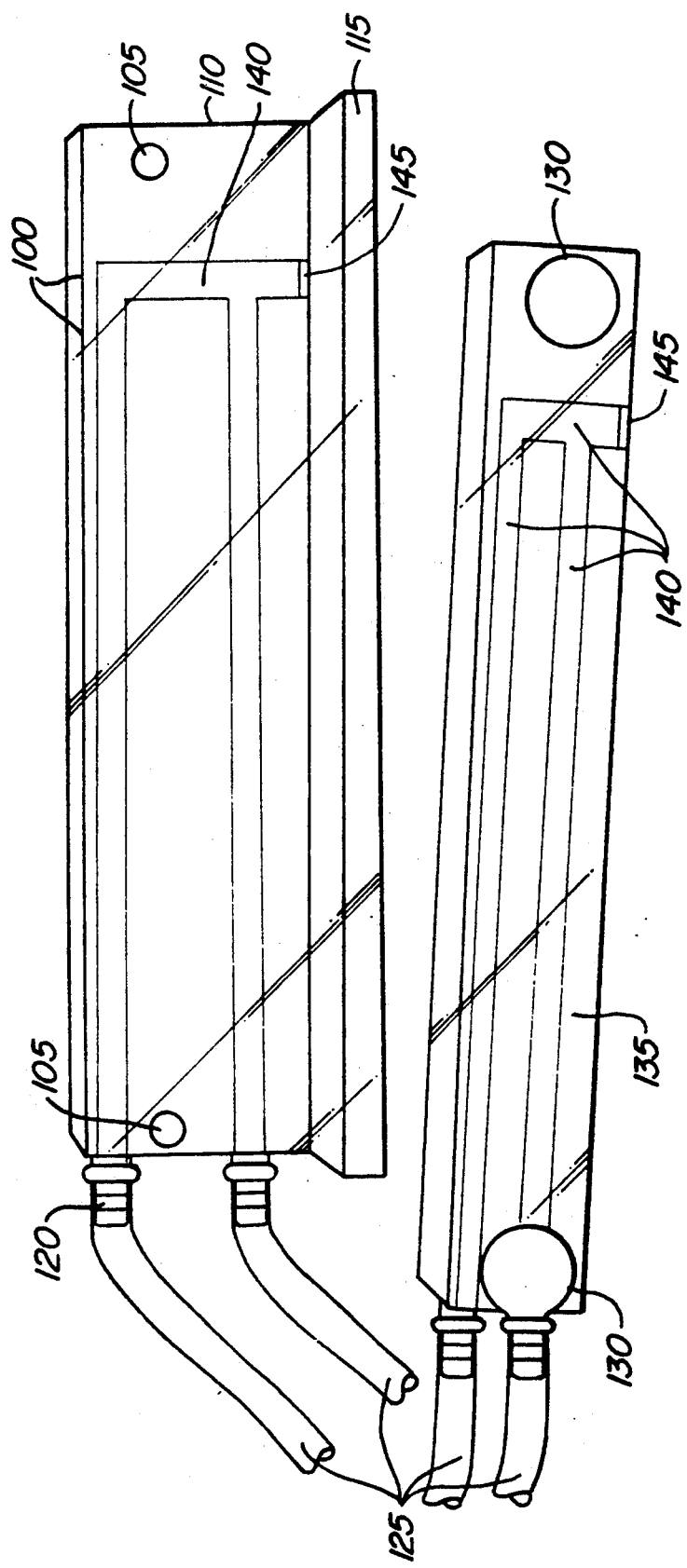
FIG. 3 shows only the heating unit in the same view as FIG. 2 with the fluid circulation channels outlined.

FIG. 3 shows the heating unit with the diffusion cells removed. In the preferred embodiment, the back plate 110 and front plate 135 contain fluid channels 140 for circulation of a liquid which is controlled in its temperature and flow externally by a laboratory circulating temperature control device. Fluid enters or exits the heating unit via the tubing 125 attached to the fittings 120 which are metal or plastic. In the preferred design, the connection fluid channel is drilled from the bottom of the respective plate and plugged with plug 145 of metal or plastic.

Operation of Intestinal Diffusion Cell System

Intestinal tissue segments can be mounted in the diffusion cell described in FIG. 1 by the method described in Grass and Sweetana (above). The technique used to prepare the tissue depends upon the transport properties to be examined. Generally, this requires the user to excise an appropriate piece of intestinal tissue and cut it along its mesenteric border. Once open to a flat rectangular segment, the tissue is positioned with its lumenal (mucosal) side over the mounting pins 55. The tissue is punctured by the pins as pushed flushed with the cell block 20 at the tissue opening 60. The tissue must be of large enough size to completely occlude the tissue opening 60, and fit over the pins 55 on each side. Serosal muscle layers may now be removed if desired, by teasing and pulling with a forceps. This procedure allow measurement of transport of substances across the epithelial cell layers, and not serosal musculature. It is assumed that this is closer to the in vivo situation.

Once the tissue is mounted, the two half-cells 20 are joined in the following manner. The tissue pins with mounted tissue are fitted to their matching holes 75. The joining pins 50 are also inserted into their matching holes 80. The two half-cells are pressed together by hand pressure and the locking screws 45 are tightened in their threaded shafts 40.

The complete diffusion cell with contained tissue segment is placed in the temperature control unit as shown in FIG. 2, adjacent to back plate 110 and bottom plate 115. The face plate 135 is place across the diffusion cells and tightened using knobs 130 to turn screw 150 into the threaded shaft 105 until the face plat is firmly against the diffusion cells surfaces. Fluid is circulated via the tubing 125 and fittings 120 through the temperature control unit fluid channels 140. The temperature of the control unit equilibrates to the temperature of the circulating fluid, and the diffusion cell blocks 20 equilibrate to the temperature of the adjacent temperature control unit. The temperature of the fluid within diffusion cells is controlled by the temperature of the blocks. The rate of fluid flow in the temperature control unit, and preheating or cooling of the diffusion cells before tissue mounting can quicken equilibration to the desired temperature.

Gas lines with appropriately sized fittings (not shown) are inserted into port 25 on each half-cell. An appropriate buffer solution for the particular tissue of study is filled into each half-cell. Generally, the donor reservoir 30 is similar composition to that of receiver reservoir 85 with the exception that the donor reservoir usually contains an amount of the test substance for measurement of transport through the tissue. Gas, usually 95%/5% oxygen/carbon dioxide is flowed into the gas ports 25. This creates bubbles in up-flow tube 65, driving fluid up the tube as they rise. The rate of bubbling controls the rate of fluid flow, and oxygenation of the tissue sample, by oxygenating the fluid. As fluid risen in the upflow tube 65, gravity drives fluid in the down flow tubes 85 and 70, across the tissue opening 60 and the tissue surface. Thus, gas flow also indirectly controls the degree of stagnant layer formation at the tissue surface.

In other embodiments, the tissue segment as the membrane may be replaced by a ring system for mounting corneal tissue as described for the apparatus used by Schoenwald (above). The tissue may also be replaced by a filter with cultured cells similar to that described by Hildago (above). The tissue may be replaced by synthetic membranes such as hydrogels or silicones as examples for the determination of material penetration rates in these substances.

Temperature control may be by alternate methods, such as electrical control of the temperature control block. Temperature control may also be directly in the chambers of the device, such as through the use of thermocouples.

Use of the apparatus according to this invention has many advantages. The current invention uses an external heating device which contacts a much greater area of the complete diffusion cell. This allows more uniform temperature control. This also has the additional advantage of making the device easier to clean between experiments, since the individual diffusion cells can be quickly removed and placed in a separate cleaning bath. The current invention also uses much less laboratory bench space since the devices are smaller, and the heating block can be designed to accommodate several at one time.

The current invention can incorporate any of the common mixing methods, but has the advantage that in the preferred embodiment, fluid flow can be made laminar to the tissue surface. This is very advantageous in experiments using intestinal tissue, since it is most similar to the in vivo situation, and limits the potential stagnant diffusion layers at the membrane surface. The design also allow free flow of bubbles, and prevents entrapment, especially at the tissue surface.

While the above description of the apparatus and use thereof according to this invention contains many specifies, these should not be construed as limitations on the scope of the invention, but merely as specific embodiments and examples of the use of preferred embodiments thereof. Those skilled in the art will envision many other variations within the scope of the invention. For example, skilled artisans will readily be able to change the dimensions and shapes of the various embodiments. They will also be able to make the components of various alternative materials.

What is claimed is:

1. In a diffusion cell block including a pair of half cells having aligned openings for holding a tissue section or membrane therebetween, wherein the improvement comprises forming each half cell as a rectangular block having a reservoir opening formed in one end and a recirculation path entirely within the block from the reservoir past the aligned opening, whereby a volume of fluid in the block can be recirculated past the aligned opening without flowing outside of the block.

2. An improved diffusion cell block as in claim 1, wherein at least one of the half cell blocks includes a gas inlet connected to the recirculation path to permit gas-induced circulation.

3. An improved diffusion cell block as in claim 2, wherein the gas inlet is formed through a side wall of the rectangular block.

4. An improved diffusion cell block as in claim 3, wherein each recirculation path includes an up-flow tube connected to one side of the reservoir and a down-flow tube connected to an opposite side of the reservoir wherein the gas inlet is connected to the up-flow tube and the reservoir opening is connected to the down-flow tube.

5. A diffusion cell system comprising:
   a base unit including a back plate and a detachable front plate;
   a plurality of cell blocks held between and in thermal contact with the back and front plates of the base unit, wherein each cell block includes a pair of half cells having aligned openings for holding a tissue section or membrane therebetween and means for exposing each side of the tissue or membrane to a fluid environment; and
   means for heating or cooling the back plate and the front plate of the base unit, whereby the cell blocks may be heated or cooled by conduction.

6. A diffusion cell system as in claim 5, wherein the cell blocks are arranged linearly with successive blocks contacting previous blocks to enhance heat transfer and temperature uniformity.

7. A diffusion cell system as in claim 5, wherein the means for heating or cooling comprises means for circulating a heat transfer fluid through the front plate and back plate.

8. A diffusion cell system as in claim 5, wherein each half cell is formed as a rectangular block having a reservoir opening formed in one end and a recirculation path from the reservoir past the opening.

9. A diffusion cell system as in claim 8, wherein at least one of the half cell blocks includes a gas inlet connected to the recirculation path to permit gas-induced circulation.

10. A diffusion cell system as in claim 9, wherein the gas inlet is formed through a side wall of the rectangular block.

11. A diffusion cell system as in claim 10, wherein each recirculation path includes an up-flow tube connected to one side of the reservoir and a down-flow tube connected to an opposite side of the reservoir, wherein the gas inlet is connected to the up-flow tube and the opening is connected to the down-flow tube.

12. A method for performing transport studies, said method comprising:
   placing membranes or tissue sections in a plurality of diffusion cell blocks;
   arranging the diffusion cell blocks linearly so that each block contacts at least one other block;
   heating or cooling the blocks on opposed surfaces to maintain a uniform temperature; and
   recirculating fluid entirely within the cell blocks on both sides of the membrane or tissue section, whereby the temperature of the recirculating fluid will be maintained substantially at the uniform temperature.

13. A method as in claim 12, wherein the membranes or tissue sections are placed between rectangular half-cells, with the resulting rectangular cells blocks being arranged with adjacent flat surfaces in substantially full contact.

14. A method as in claim 12, wherein the blocks are heated or cooled by contacting said opposed surfaces with heated plates.

15. A method as in claim 12, wherein the fluid is recirculated by introducing gas bubbles to one side of a recirculation loop.

* * * * *